(12) United States Patent
Nakamura et al.

(10) Patent No.: US 7,235,169 B2
(45) Date of Patent: Jun. 26, 2007

(54) METHOD AND APPARATUS FOR PURGING AND DISINFECTING WATER

(75) Inventors: Shinichi Nakamura, Osaka (JP); Kunihiko Fukuzuka, Habikino (JP); Jingo Nakazawa, Osaka (JP)

(73) Assignee: Omega Co., Ltd. (JP)

( * ) Notice: Subject to any disclaimer, the term of this patent is extended or adjusted under 35 U.S.C. 154(b) by 374 days.

(21) Appl. No.: 10/314,559

(22) Filed: Dec. 9, 2002

(65) Prior Publication Data
US 2003/0141202 A1 Jul. 31, 2003

(30) Foreign Application Priority Data
Dec. 28, 2001 (JP) .............................. 2001-402070
Oct. 8, 2002 (JP) .............................. 2002-295489

(51) Int. Cl.
*B01D 17/06* (2006.01)
*A61L 2/02* (2006.01)

(52) U.S. Cl. .................................... 205/687; 205/701

(58) Field of Classification Search ................ 205/687, 205/688, 695, 696, 701, 702, 742, 743, 751, 205/759, 761, 98–100
See application file for complete search history.

(56) References Cited

U.S. PATENT DOCUMENTS

| | | | | |
|---|---|---|---|---|
| 3,361,663 A | * | 1/1968 | Murray et al. ............... | 204/278 |
| 3,458,414 A | * | 7/1969 | Crane et al. ................ | 210/746 |
| 4,790,946 A | * | 12/1988 | Jansen ........................ | 210/748 |
| 4,992,156 A | * | 2/1991 | Silveri ...................... | 204/229.5 |
| 5,366,605 A | * | 11/1994 | Wang ........................ | 210/96.2 |
| 5,445,722 A | * | 8/1995 | Yamaguti et al. ......... | 204/228.6 |
| 5,547,542 A | * | 8/1996 | Landfors .................... | 162/29 |
| 5,861,090 A | * | 1/1999 | Clarke et al. ............... | 205/688 |
| 6,106,691 A | * | 8/2000 | Nakamura et al. .......... | 205/701 |
| 6,235,186 B1 | * | 5/2001 | Tanaka et al. .............. | 205/521 |
| 6,627,073 B2 | * | 9/2003 | Hirota et al. ............... | 210/169 |
| 6,863,798 B2 | * | 3/2005 | Nakamura et al. .......... | 205/687 |

FOREIGN PATENT DOCUMENTS

| | | |
|---|---|---|
| JP | 06-296968 | 10/1994 |
| JP | 07-048795 | 2/1995 |
| JP | 07-133206 | 5/1995 |
| JP | 07-189192 | 7/1995 |
| JP | 08-089969 | 4/1996 |

(Continued)

*Primary Examiner*—Nam Nguyen
*Assistant Examiner*—Luan V. Van
(74) *Attorney, Agent, or Firm*—Hayes Soloway P.C.

(57) ABSTRACT

An alkaline electrolyte solution is electrolyzed by a diaphragm-less electrolyzer to provide electrolytic water as purging and disinfecting water. The alkaline electrolyte solution is a mixture of at least one alkaline electrolyte selected from caustic sodium carbonate, caustic potassium carbonate, phosphorous sodium carbonate and sodium hypochlorite, and at least one neutral salt selected from sodium chloride, potassium chloride, sodium bromide and potassium bromide. The purging and disinfecting water is added to a water circulatory system. The result is that contaminants and noxious chemicals in the circulatory system are oxidation decomposed to thereby purge the circulating water, and noxious microorganisms such as germs, yeasts, fungi, and viruses, growing in the water circulatory system and causing degradation of water or development of slime are disinfected and thereby purged from the water circulatory system. The purging and infecting method can be carried out in a simple manner with minimum cost.

9 Claims, 9 Drawing Sheets

FOREIGN PATENT DOCUMENTS

| | | |
|---|---|---|
| JP | 08-176996 | 7/1996 |
| JP | 10-017413 | 1/1998 |
| JP | 11-128942 | 5/1999 |
| JP | 11-188364 | 7/1999 |
| JP | 11-207349 | 8/1999 |
| JP | 11-207350 | 8/1999 |
| JP | 11-207353 | 8/1999 |
| JP | 2000-046793 | 2/2000 |
| JP | 2000 140889 | 5/2000 |
| JP | 2000-256993 | 9/2000 |
| JP | 2001-114611 | 4/2001 |
| JP | 2001-347270 | 12/2001 |
| JP | 2002-126740 | 5/2002 |

\* cited by examiner

METHOD AND APPARATUS FOR PURGING AND DISINFECTING WATER

BACKGROUND OF THE INVENTION

1. Field of the Invention

The present invention relates to a method and apparatus for purging and disinfecting water for use in an air-conditioning system or a waste-gas scrubber; combined treatment water for recycling drainage water; water in which a water-soluble cutting oil, a water-soluble grinding oil, a water-soluble plastic oil, a coolant, etc. is dissolved for metal-working treatment; rinsing water for use in metal coating or surface treatment; water for use in sizing warp yarns of woven cloth; water for treating non-woven cloth; hydrophilous reaction water for emulsion polymerization and pearl polymerization; water for use in processes in a pulp plant or a papermaking plant; hot spring water; medicinal bath water; and pool water or other water for use in a plant, home, or public facility environment for humans or animals, such as a medical center or a food manufacturer. The invention is also useful in purging soil contaminated with agrichemicals, trichloro-ethylene, or dioxin, which are harmful to humans and animals.

2. Description of the Related Art

In the described field of the invention, heretofore, various methods using noxious microorganism-eradicating chemicals, such as chlorine-group, bromine-group and fluorine-group chemicals, sodium hypochlorite, ozone, hydrogen peroxide, or ultra-violet rays have been employed to kill microorganisms—such as germs, yeasts, fungi, and viruses, growing in a water circulation system and causing the degradation of water quality and the development of slime in circulating water. However, there has not yet been provided any inexpensive, useful method that has a wide spectrum of killing germs, yeasts, fungi, and viruses without producing drug-resistant microorganisms.

As the circulating water becomes dirty, the circulating water pipeline and water bath also become dirty and, as a result, an organic film is formed on the pipeline and bath walls, so that an adequate disinfections effect is difficult to achieve even when chemicals are put into the circulating water. Further, organic floaters adhere to the organic film so that microorganisms breed in the organic floaters and act as nutrients to form slime, causing clogging of the pipeline. As another problem, the slime when peeled off the pipeline walls could contaminate prospective products being processed.

The last-mentioned problem is particularly serious with the process of manufacturing paper pulp, during which a large volume of water is circulated and microorganisms, such as pulp organisms and yeasts in the pulp slurry tend to breed therein. The slime developed in the pulp slurry or white liquor in the water circulation system could be peeled off the system walls and cause drawbacks, such as staining, loss of paper product and/or breakage of a continuously traveling sheet. In many conventional methods, noxious-microorganism-eradicating chemicals, such as chlorine, bromine, fluorine, hydantoin, isothiazolon, glutaraldehyde, ozone, hydrogen peroxide, or ultraviolet rays are used. However, their operating cost is high and they are not entirely effective. Further, since part of the circulating water is drained, it could influence microorganisms in the drain water. Therefore, it would be necessary to use a moderate inhibitor rather than an antibacterial agent or fungicide disinfecting microorganisms, such as germs, yeasts, or fungi, which cause degradation of the drain water or the development of slime.

The present inventors filed the following patent applications for methods and apparatuses for purging and disinfecting pool water, bath water, water of 24-hour-open bath, fish pond water, pond water, air-conditioning water, car-wash drainage water, or combined treatment water, by electrolysis:

(1) Japanese Patent Application No. H05-087676 for apparatus for purging pool water or bath water;
(2) Japanese Patent Application No. H06-233739 for water purging method and apparatus;
(3) Japanese Patent Application No. H09-299084 for water quality purging method and mechanism;
(4) Japanese Patent Application No. H09-369487 for an electrolyzer;
(5) Japanese Patent Application No. H10-014089 for a water quality purging mechanism;
(6) Japanese Patent Application No. H10-016752 for a water quality purging mechanism;
(7) Japanese Patent Application No. H10-030555 for method and apparatus for purging water or drainage water;
(8) Japanese Patent Application No. H10-223702 for system for assessing dirt in water;
(9) Japanese Patent Application No. H10-340973 for combined treatment system and apparatus for purging combined treatment water;
(10) Japanese Patent Application No. 2000-168578 for an electrolyzer;
(11) Japanese Patent Application No. 2000-328779 for apparatus for purging water;
(12) Japanese Patent Application No. 2001-323356 for method and apparatus for treating wastewater or drainage water; and
(13) Japanese Patent Application No. 2001-369794 for an electrolyzer.

According to applications (1) and (2), although it is possible to purge and disinfect pool water or bath water by electrolysis using a titanium electrode plated with platinum, which is most resistant to corrosion, as the anode of an electrolyzer, the electrolyzing voltage would rise significantly in a short time if the electrolyzing load is large. According to application (5), by using a ferrite anode with a novel terminal-joining technique, it is possible to achieve a service life three-to-five times longer than when a platinum-plated titanium electrode is used under the same conditions.

According to applications (10) and (11) above, it is possible to provide a water-purging and disinfecting apparatus in the form of a compact, reliable electrolyzer which is easily attachable in a small environment, such as an existing bathtub or an ornamental fish tank. When the current value is increased in order to achieve a further-enhanced purging and disinfecting effect, terminals can be prevented from heating up. According to application (12) above, it is possible to provide a method and apparatus for treating waste water or drainage water containing agrichemicals, dioxin, etc.

According to these prior applications, some of the water or drainage water is introduced directly into the inter-electrode passageway (inter-electrode reaction section) of the electrolyzer so that organisms in the introduced water are oxidation decomposed to enhance the purging and disinfecting effect. However, these prior methods are not useful if water-soluble organisms essential to the processing water exist in the water. Another problem with the prior methods is that ordinary antibacterial agents or fungicide now in use would remain in the drainage water when added to the processing water, thus affecting microorganisms during a subsequent process for organisms in the drainage water.

Accordingly, there has been a need for an inexpensive, useful method which has a wide applicability for disinfecting microorganisms, such as germs, yeasts, fungi, and viruses growing in the water circulation system and causing degradation of water quality and the development of slime; and which can disinfect noxious microorganisms, such as germs, yeasts, fungi, and viruses, without giving rise to drug-resistant organisms and affecting any necessary chemicals, additives, etc. and can purge the water circulation system of such noxious microorganisms.

SUMMARY OF THE INVENTION

The present invention is particularly useful when used to purge and disinfect water for use in an air-conditioning system or a waste-gas scrubber; combined treatment water for recycling drainage water; water in which a water-soluble cutting oil; a water-soluble grinding oil, a water-soluble plastic oil, a coolant, etc. is dissolved for metalworking treatment; rinsing water for use in metal coating or surface treatment; water for use in sizing warp yarns of woven cloth; water for treating non-woven cloths; hydrophilous reaction water for emulsion polymerization and pearl polymerization; water for use in processes in a pulp plant or a papermaking plant; hot spring water; medicinal bath water; pool water; or other water for use in a plant, home, or public facility environment for humans or animals, such as a medical center or a food manufacturer.

The present invention is applicable to a wide variety of environments where water is used. Partly because additives, starch, chemicals, preservatives, etc. are added to water and partly because water-soluble organisms, such as natural or artificial substances, dirt, or sweat washed out from human bodies exist in spring water, medicinal bathwater, pool water, bath water, or the like, an environment is formed where microorganisms, such as germs, yeasts, fungi, and viruses causing degradation of water quality and development of slime tend to breed.

It is an object of the present invention to provide a method and apparatus for killing microorganisms in circulating water and purging dirt and organic film adhering to the water circulation system as the breeding ground of microorganisms, slime, etc.

To attain the above-mentioned object, the present invention takes the following measures:

(a) An alkaline electrolyte solution made by mixing sodium hypochlorite, sodium chloride, and sodium bromide is electrolyzed by a diaphragmless electrolyzer to thereby provide electrolytic water as purging and disinfecting water, and the provided purging and disinfecting water is used, with or without dilution with service water or other water to be purged and disinfected. Partly because the provided purging and disinfecting water is alkaline and partly because chlorine ions and bromine ions play a high synergistic effect when their rate is within a range of 9:1, it is possible to enhance the purging and disinfecting effect. Further, it is possible to provide purging and disinfecting water that causes no corrosion of metal parts of the water circulation system and is harmless to the human body.

(b) An alkaline electrolyte solution made by mixing sodium hypochlorite and sodium chloride is electrolyzed by a diaphragmless electrolyzer to thereby provide electrolytic water as purging and disinfecting water, and the provided purging and disinfecting water is added to the circulating water in the water circulation system, so that noxious microorganisms, such as germs, yeasts, fungi, and viruses, growing in the water circulation system are disinfected and the water circulation system is purged while the resulting circulating water flows in the water circulation system. Because a swimming pool, a bath of a hospital or an assisted-living facility, and a spring bath are each already equipped with a circulating water line, the provided purging and disinfecting water can be added to the circulating water with ease.

(c) The electrolyte solution is a mixture of at least one alkaline electrolyte selected from the group consisting of caustic sodium carbonate, caustic potassium carbonate, phosphorous sodium carbonate, and sodium hypochlorite, and at least one neutral salt selected from the group consisting of sodium chloride, potassium chloride, sodium bromide, and potassium bromide. Namely, the electrolyte solution is an alkaline electrolyte solution in which halogen ions exist. The pH of the provided purging and disinfecting water is about 7.5 to about 13, which preferably depends on the intended usage.

(d) The electrolyte solution is made to flow from an electrolyte solution container into the electrolyzer located in an electrolytic water circulating line by an electrolyte solution metering pump, and the resulting electrolytic water is added to the circulating water to thereby purge and disinfect water circulation system equipment, such as a circulating water line and object equipment that uses the circulating water, in addition to the circulating water.

(e) The circulating water is water for use in air-conditioning; water for absorbing drainage water to be recycled; water in which a water-soluble cutting oil, a water-soluble grinding oil, a water-soluble plastic oil, or a coolant is dissolved for metalworking; rinsing water for use in metal coating or surface treatment; water for use in sizing warp yarns of woven cloth; water for use in non-woven cloth treatment; hydrophilous reaction water for emulsion polymerization or pearl polymerization; or water for use in processes in a pulp plant or papermaking plant.

Necessary additives, starch, chemicals, or preservatives are dissolved in the circulating water and microorganisms, such as germs, yeasts, fungi, and viruses generated in industrial processes, causing degradation and decomposition of water or development of slime, grow in the water circulatory system. Because the facility for the water circulatory system is already equipped with a circulating water line, it is very easy to electrolyze an electrolyte solution mixed of sodium hypochlorite and sodium chloride and add the provided purging and disinfecting water to the circulating water.

It is possible to purge microorganisms, such as germs, yeasts, fungi, and viruses growing in the water circulatory system and causing decomposition of water and development of slime, with hardly any effect on these added substances, and to decompose and purge dirt such as slime and organic film adhering to the water circulatory system.

(f) When activated carbon is placed on or in a filter located in the circulating water line, hypohalogenous acid and hypohalogenous acid ions remaining in the circulating water are decomposed by catalytic action to discharge activated oxygen. By such strong oxidation, it is possible to decompose and purge dirty substances and microorganisms in the circulating water, which are adhered and adsorbed to the filter and the activated carbon.

(g) Most of the existing baths, springs, and swimming pools, bath water, spring water, medicinal bathwater, and pool water are used in circulation. The electrolytic water line can be easily connected to the existing circulating water line in a short time. The electrolyte solution is made to flow from an electrolyte solution container into the electrolyzer located in an electrolytic water line by an electrolyte solution-metering pump, to thereby provide the electrolytic water as purging and disinfecting water. When the provided electrolytic water is added to the circulating water, it is possible to decompose water-soluble organisms, such as dirt removed from the human body and dissolved in the circulating water, and, at the same time, kill microorganisms, such as germs, yeasts, fungi, and viruses, to thereby purge and disinfect the water circulation system.

(h) Japanese Patent Application No. 2002-323356 for method and apparatus for processing waste water or drainage water, (12) above, and Japanese Patent Application No. 2001-369794 for an electrolyzer, (13) above, disclose methods and apparatuses in which the circulating water is soil-cleaning water for washing soil contaminated with noxious substances, such as agrichemicals, trichloroethylene, or dioxin, and the contaminated soil is washed so that the noxious substances are washed out or extracted in the soil-cleaning water, and the resulting soil-cleaning water is purged by oxidation decomposition of the noxious substances by electrolysis. The electrolyzer can purge the soil-washing water containing noxious substances, such as agrichemicals, trichloroethylene, or dioxin, whereupon the purged soil-washing water can be drained safely or recycled for the same use.

(i) The water purging and disinfecting system of the present invention comprises an electrolyte solution container for storing an alkaline electrolyte solution made by mixing sodium hypochlorite and sodium chloride; an electrolyzer for electrolyzing the electrolyte solution to thereby provide electrolytic water as purging and disinfecting water; a metering pump for forcing the electrolyte solution from the electrolyte solution container to said electrolyzer for electrolysis; and a circulating water line, composed of an electrolytic water line, object equipment that uses the circulating water, a prefilter, a circulation pump, and a filter, for adding the purging and disinfecting water to the circulating water.

(j) For an anode of the electrolyzer, a pipe of nickel ferrite, which is inexpensive, has comparatively good conductivity as conductive ceramics and is most resistant to corrosion, or a nickel ferrite rod having an axial hole, or a tubular electrode coated with nickel ferrite is used. Such anodes and cathodes in the form of corrosion-resistant and conductive metal tubes are concentrically arranged alternately with inter-electrode distances ranging from 1.1 mm to 9 mm. An electrolyte solution is diluted with well water or service water or mixed or diluted with processing water, whereupon the resulting water is made to flow into the inter-electrode spaces. The electrolytic water is then continuously added to the water circulatory system.

DETAILED DESCRIPTION OF THE PREFERRED EMBODIMENTS

A preferred embodiment of the present invention will now be described with reference to FIG. 1, which is a flow chart illustrating the manner in which water or the like is purged and disinfected. Water to be used in object equipment 10 is water for use in air-conditioning, water for use in a waste gas scrubber, water for combined treatment water to be recycled, water in which a water-soluble cutting oil, a water-soluble grinding oil, a water-soluble plastic oil or a coolant is dissolved for metalworking, rinsing water for use in metal coating or surface treatment, water for use in sizing warp yarns of woven cloth, water for use in non-woven cloth treatment, hydrophilous reaction water for emulsion polymerization or pearl polymerization, water for use in processes in a pulp plant or papermaking plant, pool water, spring water, or medicinal bathwater.

Figure 1:
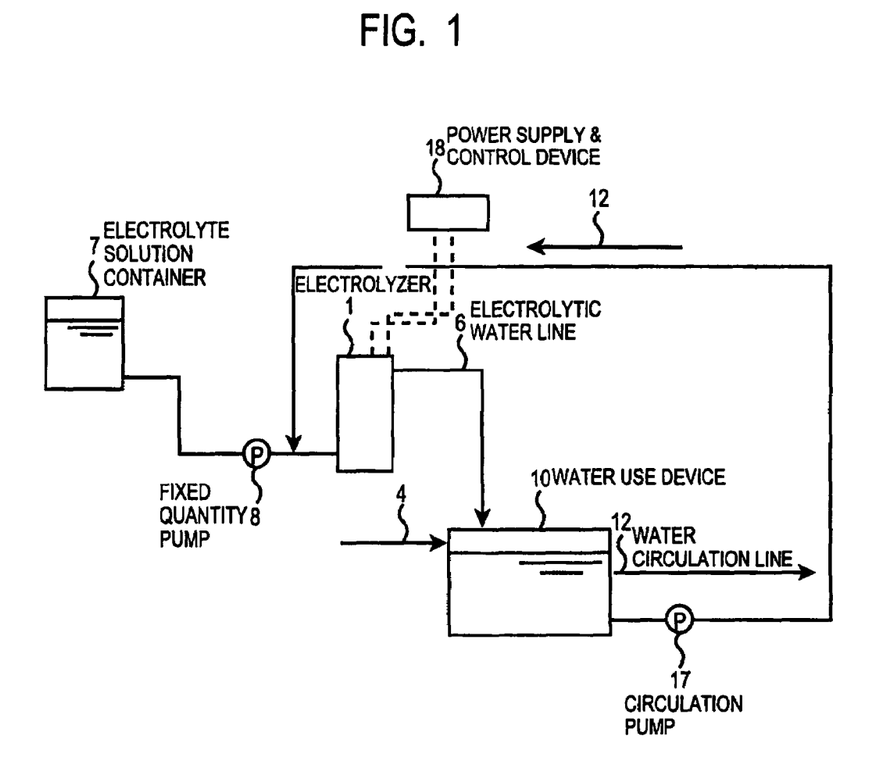
FIG. 1 is a flow sheet illustrating the manner in which circulating water is purged and disinfected.

A circulating water line 12 shown in FIG. 1 is comprised of the object equipment 10, a prefilter 13, a circulation pump 17, a filter 14, and a heat exchanger 9. In an electrolytic water line 6, the electrolyte solution of an electrolyte solution container 7 is metered out by an electrolytic solution metering pump 8 so that the electrolyte solution is diluted with a constant amount of circulating water led from the circulating water line 12 by a bypass to thereby provide electrolytic water in inter-electrode passageways (inter-electrode reaction section) of an electrolyzer as purging and disinfecting water having a strong oxidizing and disinfecting effect. The provided purging and disinfecting water is supplied to the circulating water line 12 via the electrolytic water line 6.

EXAMPLE 1

The water purging and infecting apparatus according to the present invention was installed at each of four hotels in Kinosaki Onsen (Hot Spring Resort), Japan, and hot-spring water quality tests were conducted, as hot-spring water was recycled. Over 60% of hot springs in Japan use circulating hot-spring water. When many people use a single hot-spring-water bath, the hot-spring water becomes dirty. As coliform bacillus and other bacteria breed, microorganisms increase in dirty matter adhered to walls of the circulating water line 12, causing development of slime and organic film. Amoebas, who are an intermediate host of the *Legionella bacillus*, use these microorganisms as food. Reportedly, the number of people attacked by *Legionella bacillus* in hot spring resorts is on the increase in recent years, and some people died of Legionnaires' disease. In the meantime, it has been the common practice to use chlorine as a disinfectant, but chlorine gives off a very unpleasant smell.

Figure 2:
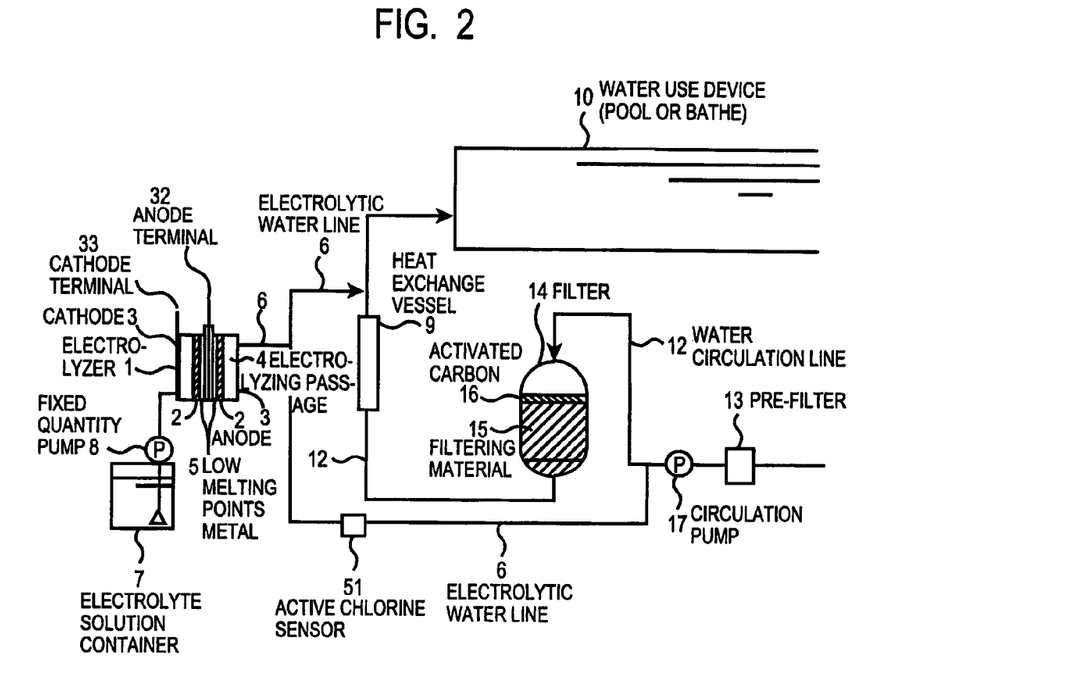
FIG. 2 is a flow sheet illustrating the manner in which pool water and bath water are purged and disinfected.
Figure 3:
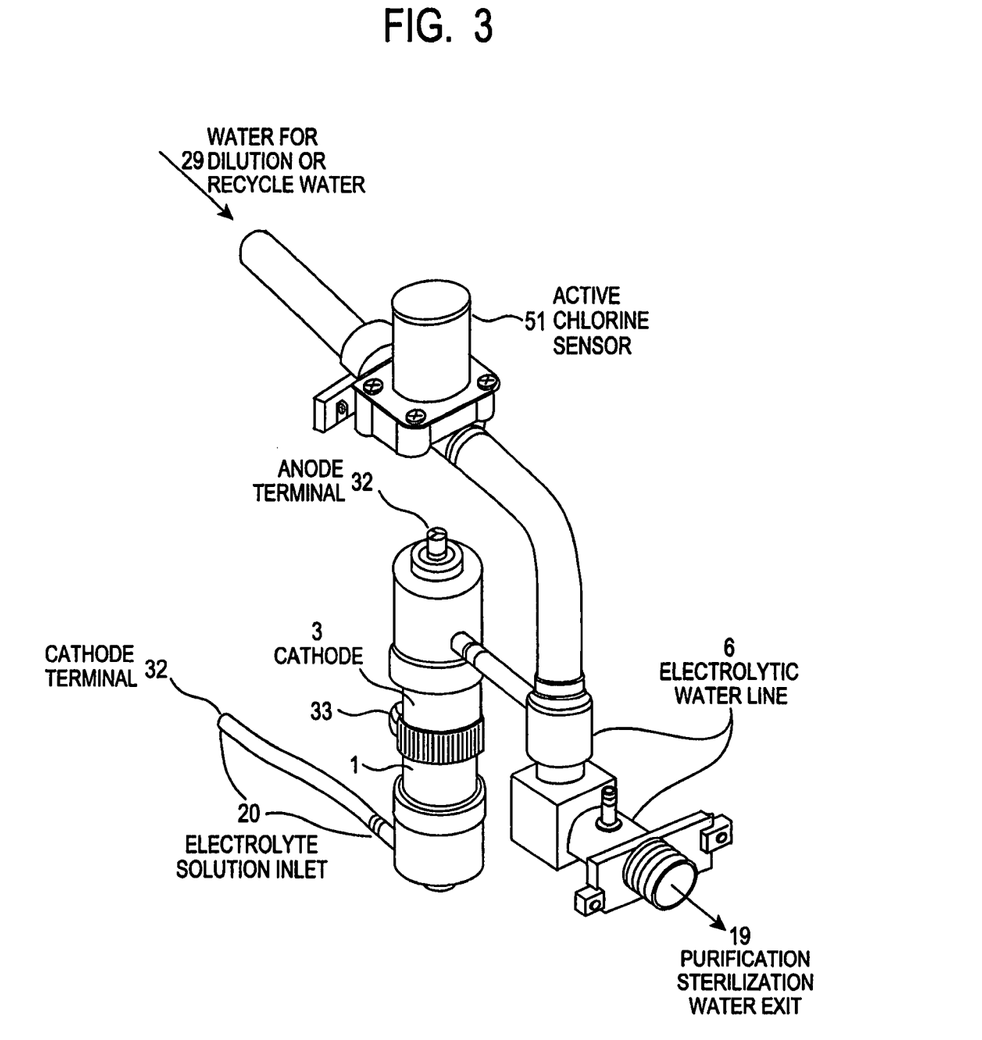
FIG. 3 is a perspective view of an electrolyzer and a residual salt sensor in an electrolytic water line.

FIG. 2 is a flow diagram illustrating the manner in which hot-spring water was purged and infected is used in a hot-spring bath or pool. The circulating water line 12 equipped with the filter 14 was already installed in each hotel. The object equipment 10 on which the present test operations took place is comprised of a men's bath and a ladies' bath, each containing hot-spring water of about 4 m$^3$ and 8 m$^3$ in total, and the amount of circulating flow is 16 m$^3$/hour. The electrolytic water line 6, which is very compact as shown in FIG. 3, was connected to the existing circulating water line 12 as a bypass branched therefrom. Part of the circulating water was introduced into the electrolytic water line 6, and residual salt (residual chlorine) concentration was measured by a residual salt sensor 51.

With the residual salt (residual chlorine) concentration set at a predetermined value, the electrolyzer 1 and the electrolyte solution metering pump 8 were operated to carry out electrolysis, thereby providing the electrolytic water as purging and disinfecting water and adding the provided purging and disinfecting water to the circulating water in the electrolytic water line 6. This purging and infecting water merged into the circulating water in the circulating water line 12, and the mixed water was returned to the object equipment 10 as recycled water. While the circulating water was thus repeatedly used, the residual salt (residual chlorine) concentration was kept constant at the predetermined value.

An alkaline electrolyte solution was prepared by adding sodium chloride to a commercially available 12% sodium hypochlorite solution. The alkaline electrolyte solution was used in the electrolysis. The amount of added sodium chloride was adjusted commensurate with the hot-spring water quality. Table 1 shows the test results. During the first four (testing) days, the conventional electrolyte solution mixed of chlorine and commercially available 12% sodium hypochlorite was used. From the fifth day onward, the subject electrolyte solution according to the present method was used. On the sixth day, 100 CFU/100 ml of *Legionella bacillus* count was found, and consequently, the residual salt (residual chlorine) concentration value of the residual salt sensor 11 was set to a slightly higher value than the initial preset value for subsequent tests. Test data were collected at men's and ladies baths in four hotels, and part of the test data is shown in Table 1.

TABLE 1

Hotel A, Gentlemen-use baths of 4 m$^3$ × 2, amount of circulating water flow of 16 m$^3$/hour, Kinosaki Onsen (Hot Spring Resort), hot-spring water: containing chloride earth metal, low salt, spa with high level of relaxing hypotonics

| Test day | day | Comparative Example | | | | Example 1 | | | |
|---|---|---|---|---|---|---|---|---|---|
| | | 1 | 2 | 3 | 4 | 5 | 6 | 7 | 8 |
| pH | | 7.80 | 7.5 | 7.6 | 7.7 | 7.9 | 8.1 | 7.9 | 7.7 |
| electric conductivity | IS/cm | 5.230 | 4.150 | 4.980 | 5.120 | 4.960 | 4.270 | 4.220 | 4.850 |
| consumed KMNO$_4$ | mg/l | 9.45 | 8.63 | 6.98 | 9.48 | 5.32 | 5.25 | 5.63 | 5.10 |
| coliform bacillus | MPN/10 Qml | 1 | 7.8 × 10 | 2 | 1 | 1 | 0 | 0 | 0 |
| bacteria | CFU/ml | 2.3 × 10$^2$ | 1.04 × 10$^4$ | 7 × 10$^2$ | 2 × 10$^3$ | 1 × 10$^2$ | 1.2 × 10 | 1.6 × 10 | 1.1 × 10 |
| Legionella bacillus | CFU/100 ml | — | 100 | — | — | — | 100 | — | 10 |
| ammoniacal nitrogen | mg/l | 1.20 | 2.32 | 1.56 | 1.20 | 1.11 | 0.85 | 0.62 | 0.68 |
| residual chlorine | mg/l | 0.38 | 0.39 | 0.42 | 0.52 | 0.18 | 0.21 | 0.17 | 0.19 |
| chlorine smell | | present | present | present | strong | absent | absent | absent | absent |
| slime on bottom | | yes | yes | yes | abundant | yes | yes | no | no |

| | | present method 2 | | | | Ministry of Health and Welfare (MHW) bathwater standards | |
|---|---|---|---|---|---|---|---|
| Test day | day | 9 | 10 | 11 | 12 | | public bath/spa |
| pH | | 7.8 | 7.9 | 7.7 | 7.9 | pH | 5.8–9.6 |
| electric conductivity | IS/cm | 5.140 | 4.790 | 4.650 | 4.850 | electric conductivity | |
| consumed KMNO$_4$ | mg/l | 4.11 | 3.56 | 3.12 | 2.31 | consumed KMNO$_4$ | 25 ng/liter or less |
| coliform bacillus | MPN/10 Qml | 0 | 0 | 0 | 0 | coliform bacillus | 1/nL or less |
| bacteria | CFU/ml | 6 | 3 | 1 | 1 | bacteria | |
| Legionella bacillus | CFU/100 ml | — | 10 | — | 0 | Legionella bacillus | less than 10 CFU/100 ml |
| ammoniacal nitrogen | mg/l | 0.54 | 0.32 | 0.23 | 0.18 | ammoniacal nitrogen | 1 mg/liter or less |

TABLE 1-continued

Hotel A, Gentlemen-use baths of 4 m³ × 2, amount of circulating water flow of 16 m³/hour, Kinosaki Onsen (Hot Spring Resort), hot-spring water: containing chloride earth metal, low salt, spa with high level of relaxing hypotonics

| | | | | | | | | |
|---|---|---|---|---|---|---|---|---|
| residual chlorine | mg/l | 0.28 | 0.28 | 0.28 | 0.26 | residual chlorine | 0.2–0.4 ng/liter |
| chlorine smell | | absent | absent | absent | absent | | |
| slime on bottom | | no | no | no | no | | |

NB (Nash Box): Preferably, chlorine group disinfectant to be used should be such that separate/residual chlorine concentration in bath water is kept at 0.2-0.4 ng/liter for over 2 hours a day.

EXAMPLE 2

Figure 4:
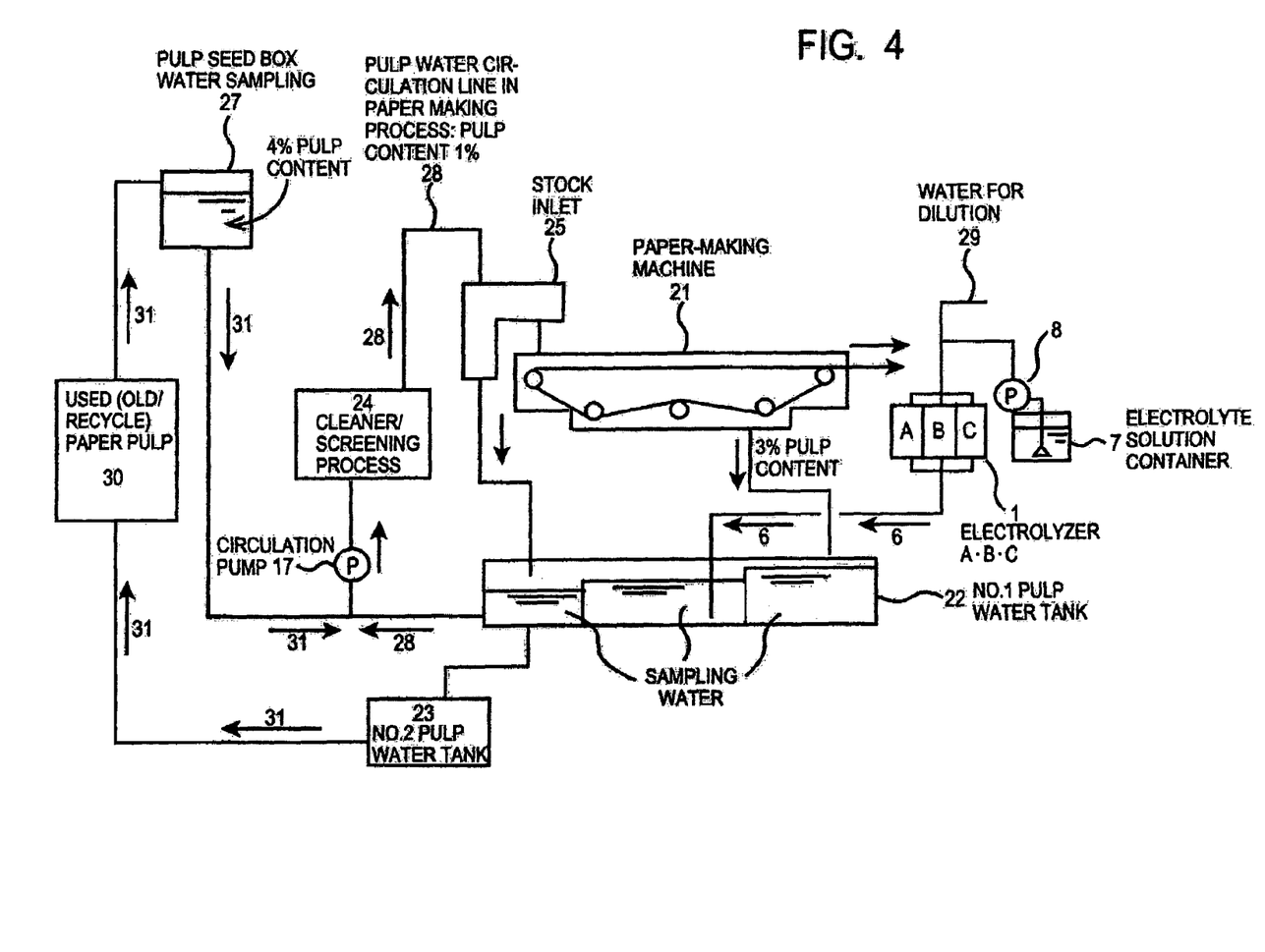
FIG. 4 is a flow sheet illustrating the manner in which a white liquor circulating line is purged and disinfected in a recycling papermaking process by a water purging and disinfecting apparatus incorporated in the circulating line.

FIG. 4 is a flow diagram illustrating the manner in which circulating white liquor was purged and disinfected as used in a white liquor circulating line 28 of a paper sheeting station at a papermaking plant. White liquor of 3.5% pulp concentration introduced into a pulp seed box 27 via a main white-liquor circulation line 31 was supplied to the white liquor circulating line 28 of the paper sheeting station so as to regulate the pulp concentration of the post-paper-sheeting circulating liquor to a reference of 1%. Then the paper sheeting took place using a paper sheeting machine 21 as the white liquor traveled through a cleaner, a screener 24 and a stock inlet 25. The post-paper-sheeting white liquor was repeatedly circulated by the white liquor circulating line 28 via a first white liquor tank 22. In the conventional method, a slime prevention agent (Slicon) was used in an attempt to avoid the occurrence of problems in the paper sheeting station due to slime of the circulating white liquor in the white liquor circulating line 28. Since the slime prevention agent increased non-biodegradable wastage and hairline, clean-up had to be performed often and, in the worst case, the operation of the object equipment had to be stopped often.

Figure 5A:
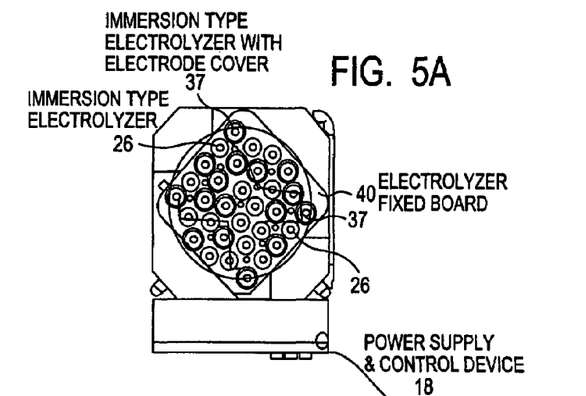
FIGS. 5A, 5B and 5C are a set of views showing a water purging and disinfecting test apparatus in which 32 dipping electrolyzers are arranged in a synthetic resin electrolytic bath.
Figures 5B, 5C:
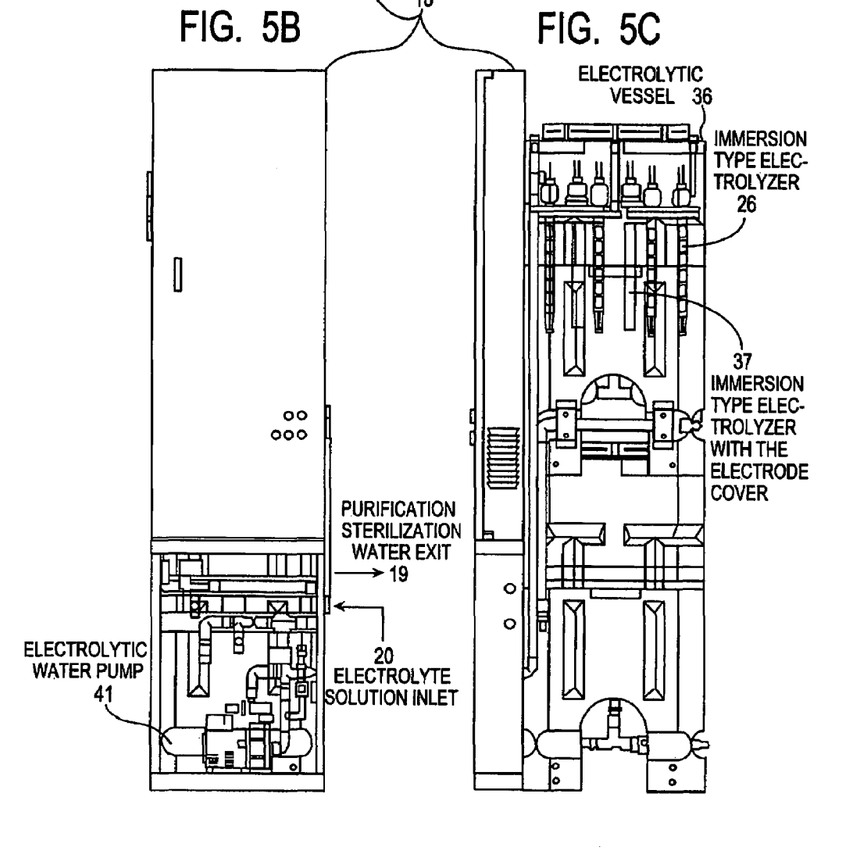
Figure 6:
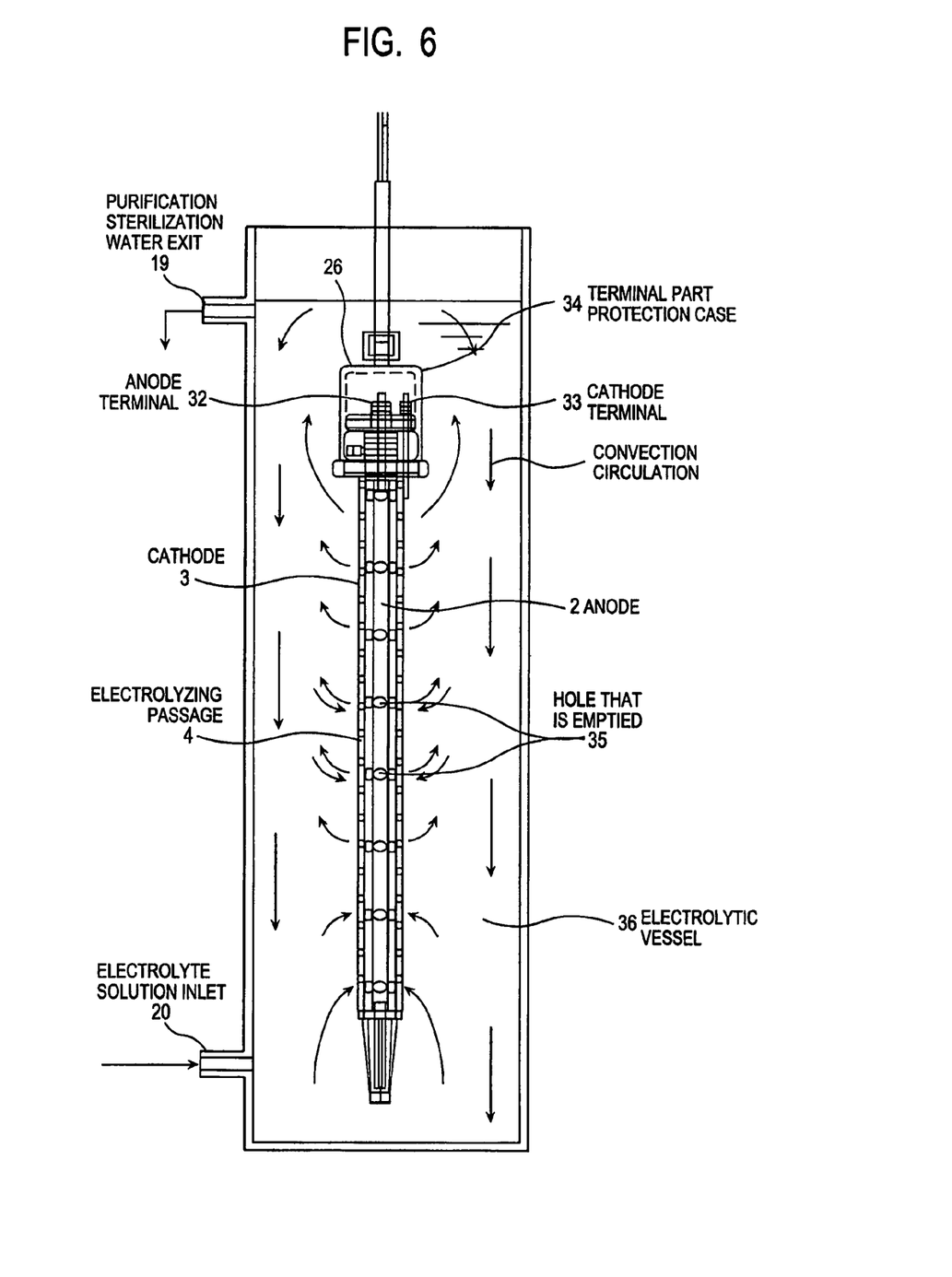
FIG. 6 is a side view of the individual dipping electrolyzer dipped in the water in the electrolytic bath for electrolysis.
Figure 7:
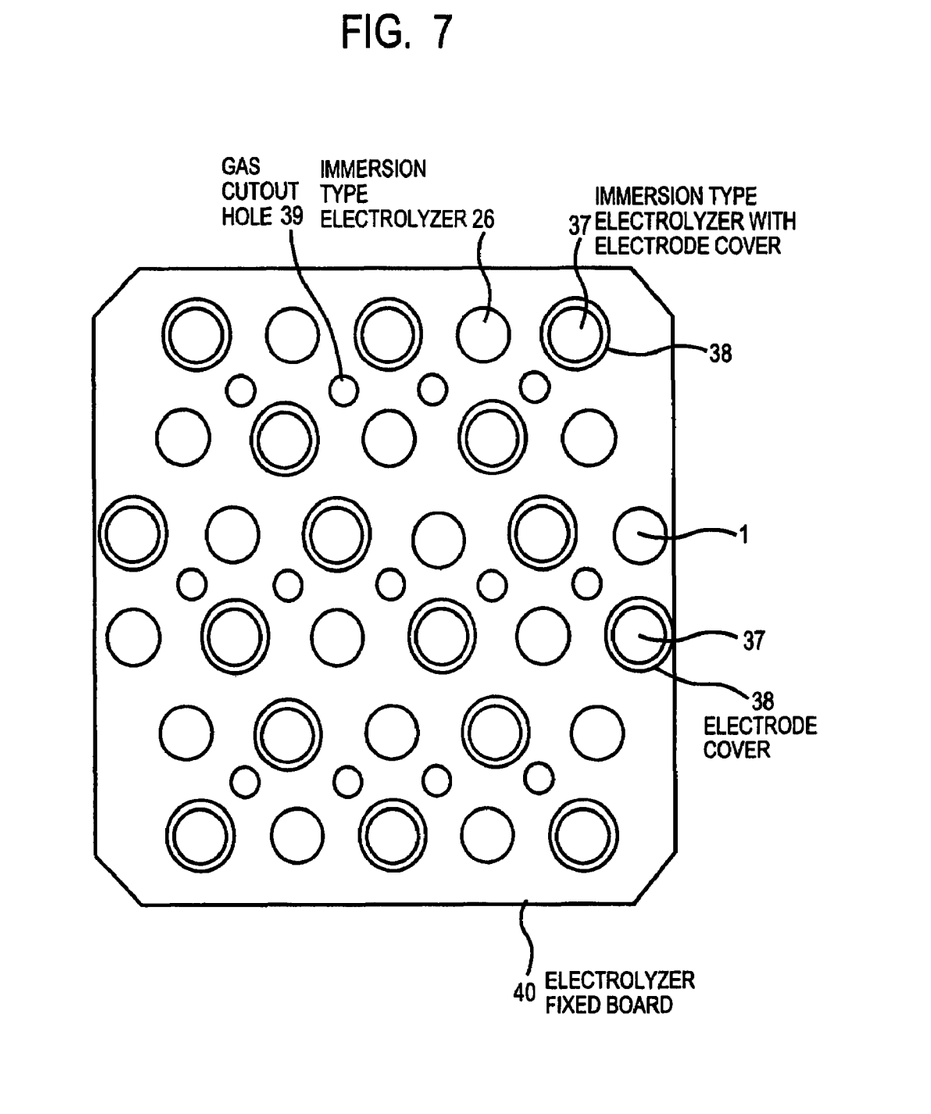
FIG. 7 is a schematic top plan view showing the plural dipping electrolyzers and a plurality of dipping electrolyzers with electrode covers arranged in the electrolytic bath.

FIGS. 5A, 5B and 5C are a set of top, front and side views of a purging and disinfecting testing apparatus (manufactured by GES Inc.). Thirty-two (32) immersion-type electrolyzers 26 of FIG. 6 were arranged in a synthetic resin electrolytic vessel 36, as shown in FIG. 7. FIG. 6 shows only one immersion-type electrolyzer 26 dipped in the water in the electrolyte vessel 36. The holed cathode 3 introduced water into the bath and discharged the water from the bath to be electrolyzed by the airlift action of gas generated during the electrolysis, thus convecting the water to be electrolyzed. The overall design of the synthetic resin electrolytic vessel (purging and disinfecting tank) 36 was registered as Japanese Design Application No. H11-013620.

A single purging and disinfecting testing apparatus has an operating power corresponding to 220 m³/hour of circulating white liquor (pulp suspension solution). Since the amount of flow of the white liquor circulating line 28 in the paper sheeting station is 220 m³/hour, three identical testing apparatuses were used. As shown in FIG. 4, each of the three purging and disinfecting testing apparatuses was equipped with thirty-two (32) immersion-type electrolyzers 26, being comprised of the electrolytic vessel 36, an electrolytic water pump 41, and a power-source/controller, which are joined together as a unit. Each immersion-type electrolyzer 26 was set to 500 iS/cm of specific conductance at 12 A and 9V. 3 liters/hour of the electrolyte solution were quantitatively added to and mixed with 1 m³/hour of well water from the electrolyte solution container 7. 9 m³/hour of the total electrolytic water in the electrolytic vessel 36 were moved to the first white liquor tank of the white liquor circulating line 28 by the electrolytic water pump 41.

In Example 2, 5%-3% by weight of sodium chloride was added to a commercially available solution of 12% by weight sodium hypochlorite to prepare an alkaline electrolyte solution. In the case of 4% by weight of sodium chloride, the well-water dilution before being introduced into the electrolyzer was 9.5 in pH, 1500iS/cm in specific conductance, and 280-300 mg/liter in residual chlorine concentration. On the other hand, the electrolytic water was 9.7 in pH, and 350-370 mg/liter in residual chlorine concentration. Thus the residual chlorine concentration increased by an average of 50 mg/liter.

Beginning December 6, a test was conducted in the white liquor circulating line 28 of the paper sheeting station. Test data collected during 11 days from starting operation of the present testing apparatus and also before starting operation are shown in Table 2. Table 2 indicates that, after the operation of the present testing apparatus was started, clean-up was carried out twice at the beginning and only once on December 20 (not shown), and since then until December 27 (not shown), no clean-up was necessary.

TABLE 2

| | date | patch rate (a) | NB rate (b) | hairline rate (c) | Silicon rate (d) | product number | coupling number (e) | patch number | coupling rate (f) | NB waste (g) | long narrow hole(s) | others |
|---|---|---|---|---|---|---|---|---|---|---|---|---|
| | November | | | | | | | | | | | |
| | 1 | 4.3% | 1.4% | 3.6% | 100% | 140 | 6 | 6 | 4.3% | 2 | 5 | |
| | 2 | 6.8% | 1.4% | 6.8% | 100% | 146 | 10 | 10 | 6.8% | 2 | 10 | |
| | 3 | 0.8% | 0.0% | 1.5% | 100% | 133 | 4 | 1 | 3.0% | 0 | 2 | Clean up |
| | 4 | 0.8% | 0.0% | 0.8% | 100% | 132 | 8 | 1 | 6.1% | 0 | 1 | |
| | 5 | 2.1% | 0.0% | 2.9% | 100% | 140 | 12 | 3 | 8.6% | 0 | 4 | |
| | 6 | 0.0% | 0.0% | 0.0% | 100% | 99 | 0 | 0 | 0.0% | 0 | 0 | Clean up |
| | 7 | 1.5% | 0.0% | 1.5% | 100% | 137 | 10 | 2 | 7.3% | 0 | 2 | |
| | 8 | 4.9% | 0.0% | 4.2% | 100% | 144 | 4 | 7 | 2.8% | 0 | 6 | |
| | 9 | 9.4% | 1.4% | 5.8% | 100% | 138 | 5 | 13 | 3.6% | 2 | 8 | Clean up |
| | 10 | 2.2% | 0.0% | 2.2% | 100% | 139 | 8 | 3 | 5.8% | 0 | 3 | |
| | 11 | 6.3% | 0.0% | 5.6% | 100% | 142 | 6 | 9 | 4.2% | 0 | 8 | |
| | 12 | 20.6% | 1.4% | 17.7% | 100% | 141 | 9 | 29 | 6.4% | 2 | 25 | |
| | 13 | 0.0% | 2.1% | 2.1% | 100% | 48 | 0 | 0 | 0.0% | 1 | 1 | Clean up |
| | 14 | 2.5% | 1.7% | 0.0% | 100% | 120 | 20 | 3 | 16.7% | 2 | 0 | Clean up |
| | 15 | 0.7% | 0.0% | 5.0% | 100% | 148 | 8 | 1 | 5.4% | 0 | 0 | |
| | 16 | 1.4% | 0.7% | 1.4% | 100% | 142 | 8 | 2 | 5.6% | 1 | 2 | |
| | 17 | 7.7% | 3.8% | 3.1% | 100% | 130 | 13 | 10 | 10.0% | 5 | 4 | Clean up |
| | 18 | 10.6% | 2.4% | 8.2% | 100% | 85 | 1 | 9 | 1.2% | 2 | 7 | Clean up |
| | 19 | 0.0% | 0.0% | 0.0% | 100% | 90 | 1 | 0 | 1.1% | 0 | 0 | Clean up |
| | 20 | 1.4% | 0.7% | 2.1% | 100% | 144 | 7 | 2 | 4.9% | 1 | 3 | |
| | 21 | 2.1% | 0.7% | 2.1% | 100% | 142 | 6 | 3 | 4.2% | 1 | 3 | |
| | 22 | 14.3% | 6.4% | 9.3% | 100% | 140 | 5 | 20 | 3.6% | 9 | 13 | |
| | 23 | 9.4% | 2.2% | 6.5% | 100% | 138 | 2 | 13 | 1.4% | 3 | 9 | Clean up |
| | 24 | 9.0% | 1.4% | 8.3% | 100% | 144 | 5 | 13 | 3.5% | 2 | 12 | |
| | 25 | 10.2% | 3.9% | 7.9% | 100% | 127 | 6 | 13 | 4.7% | 5 | 10 | Clean up |
| | 26 | 4.3% | 0.0% | 2.1% | 100% | 140 | 0 | 6 | 0.0% | 0 | 3 | |
| | 27 | 9.0% | 0.7% | 5.6% | 100% | 144 | 1 | 13 | 0.7% | 1 | 8 | |
| | 28 | 0.0% | 1.5% | 1.5% | 100% | 68 | 0 | 0 | 0.0% | 1 | 1 | Clean up |
| | 29 | 2.3% | 0.0% | 3.0% | 100% | 133 | 8 | 3 | 6.0% | 0 | 4 | |
| | 30 | 14.9% | 6.4% | 6.4% | 100% | 141 | 6 | 21 | 4.3% | 9 | 9 | |
| | December | | | | | | | | | | | |
| | 1 | 15.3% | 8.8% | 4.4% | 100% | 137 | 3 | 21 | 2.2% | 12 | 6 | Clean up |
| | 2 | 11.4% | 6.1% | 5.3% | 100% | 132 | 5 | 15 | 3.8% | 8 | 7 | |
| | 3 | 13.5% | 0.7% | 12.8% | 100% | 148 | 8 | 20 | 5.4% | 1 | 19 | |
| | 4 | 1.0% | 0.0% | 2.1% | 100% | 96 | 1 | 1 | 1.0% | 0 | 2 | Clean up |
| | 5 | 2.2% | 0.0% | 1.1% | 100% | 91 | 1 | 2 | 1.1% | 0 | 1 | |
| ↓ | 6 | 1.2% | 0.0% | 0.0% | 100% | 82 | 2 | 1 | 2.4% | 0 | 0 | Clean up |
| DB | 7 | 0.8% | 0.0% | 0.8% | 100% | 130 | 21 | 1 | 16.2% | 0 | 1 | |
| operation | 8 | 0.0% | 0.0% | 0.0% | 100% | 75 | 18 | 0 | 24.0% | 0 | 0 | Clean up |
| | 9 | 0.0% | 0.0% | 0.0% | 100% | 122 | 20 | 0 | 16.4% | 0 | 0 | |
| | 10 | 1.4% | 0.0% | 0.0% | 75% | 139 | 13 | 2 | 9.4% | 1 | 0 | |
| | 11 | 0.7% | 0.0% | 0.0% | 75% | 135 | 7 | 1 | 5.2% | 0 | 0 | |
| | 12 | 0.0% | 0.0% | 0.0% | 50% | 138 | 10 | 0 | 7.2% | | 0 | |
| | 13 | 0.7% | 0.0% | 0.0% | 50% | 141 | 2 | 1 | 1.4% | 0 | 0 | |
| | 14 | 0.0% | 0.0% | 0.0% | 25% | 141 | 2 | 0 | 1.4% | 0 | 0 | |
| | 15 | 0.0% | 0.0% | 0.0% | 25% | 158 | 0 | 0 | 0.0% | 0 | 0 | |
| | 16 | 0.0% | 0.0% | 0.0% | 0% | 158 | 0 | 0 | 0.0% | 0 | 0 | |
| | 17 | | | | 0% | | | | | | | |
| | 18 | | | | 0% | | | | | | | |

(a) "Patch rate" means the rate of patch numbers/day against total product production/day.
(b) "NB rate" means Nash box slime hold/day/total production numbers (rolls)/day.
(c) "Hairline rate" means measure of the number of long narrow holes/day/total production numbers (rolls) /day.
(d) "Silicon rate" means consumption of slime control agent (100% is usual quantity).
(e) "Coupling number" means the number of times a paper making machine is stopped to cut and repair (couple) a paper web.
(f) "Coupling rate" mans the rate of coupling numbers/day against total production numbers (rolls)/day.
(g) "NB waste" means Nash box slime holes (NB is vacuuming drier).

Figure 8:
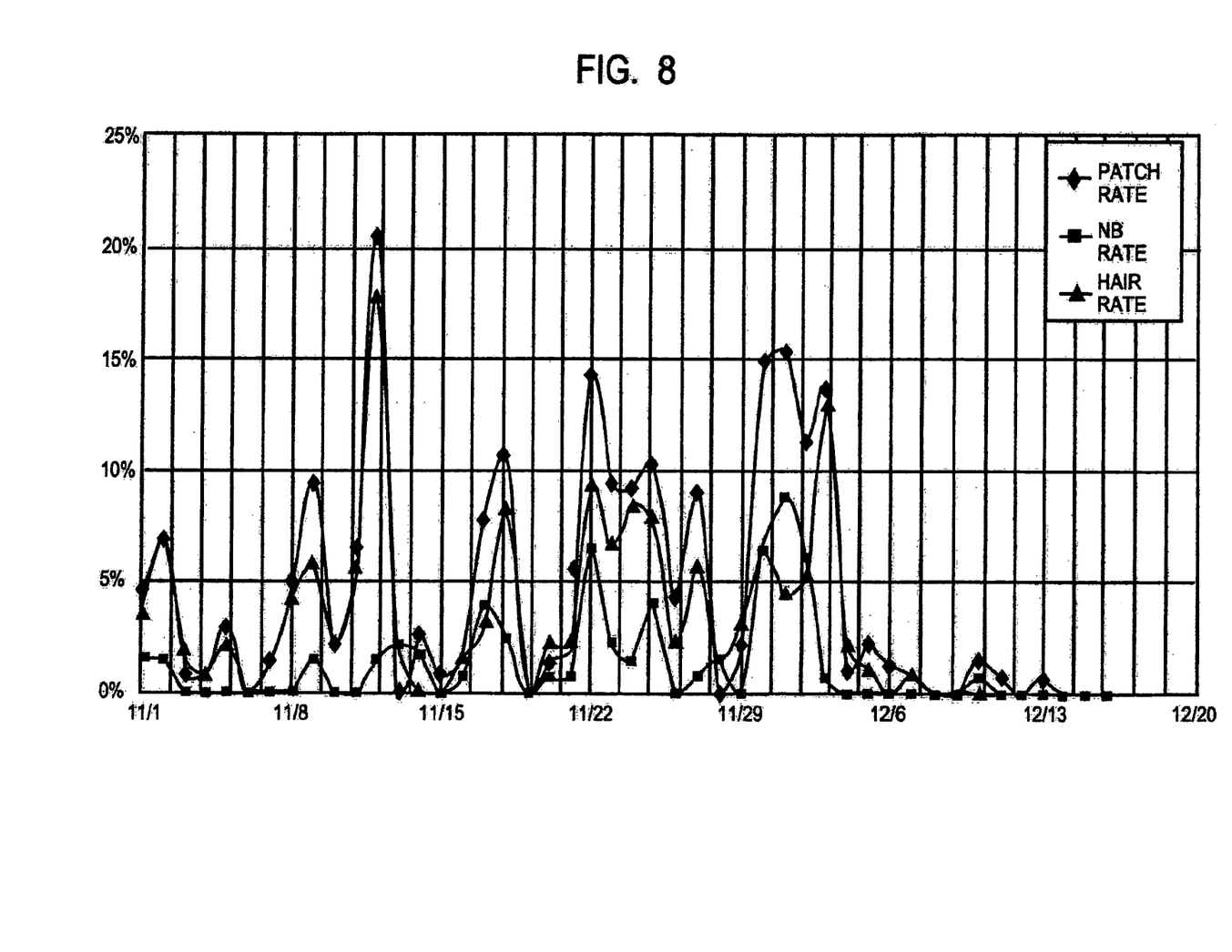
FIG. 8 is a graph showing the change in patch rate, Nash box rate, and hairline rate before starting and eleven days after starting operation of the purging and disinfecting test apparatus.

FIG. 8 is a graph showing the change in patch rate, Nash Box rate and hairline rate of Table 2. Table 2 indicates that these values changed by a large extent before the operation of the present testing apparatus was started. At the highest, patch rate changed in a range of 5-20%; non-biodegradable (NB) waste, in a range of 1 to 8%; and hair rate, in a range of 4-17%. To this end, the operation of the, object equipment had to be stopped often, and during each stop, clean-up took place to treat about 20 m³ of white liquor of the first white liquor tank 22 and about 3 m³ of white liquor of the second white liquor tank 23, these tanks being contaminated with slime or other dirty matter.

Figure 9:
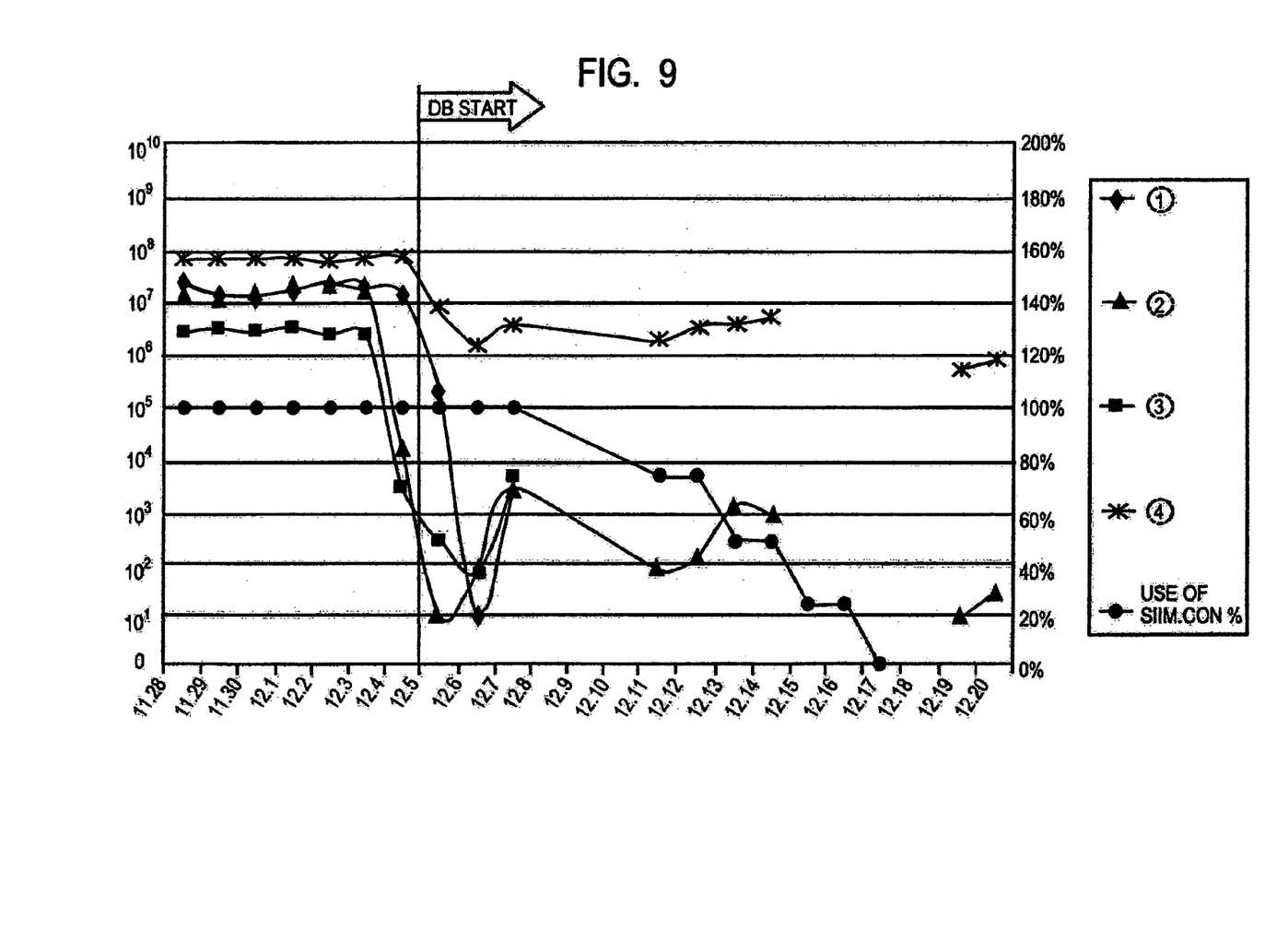
FIG. 9 is a graph showing the transition of results of microorganism count tests conducted by sampling water from the white liquor circulating line on a daily basis after operation of the water purging and disinfecting test apparatus started on December 6 and the transition of results of comparative tests conducted for comparison from November 28 before operation of the test apparatus started.

FIG. 9 is a graph showing the transition of results of microorganism count tests conducted by sampling water from the white liquor circulating line on a daily basis after operation of the water purging and disinfecting test apparatus beginning on December 6 and continued until December 20 and the transition of results of comparative tests conducted from November 28 before operation of the test apparatus started, against the amount of slime prevention agent (Slicon). The amount of added slime prevention agent before the operation of the present testing apparatus was started was regarded as 100%. On the other hand, the amount of added slime prevention agent was gradually reduced from December 6 onward, and after December 17, no slime prevention agent was added.

In the white liquor circulating line of FIG. 4, slime and other similar matter precipitated and separated in three subtanks a, b, c of the first white tank 22 in which the post-paper-sheeting white liquor was stored. Sampling for water quality examination took place at the first white liquor tank 22 and the pulp seed box 27. Raw white liquor of 4% by weight pulp concentration was fed from a de-inking station 30 (during pulping from printed paper) to the pulp seed box 27 via the major white-liquor circulation line 31. Bacteria count as measured on the white liquor sampled from the first white liquor tank 22 was $10^6$-$10^7$ CFU/ml before the operation of the testing apparatus was started but was sharply reduced to below $10^3$ CFU/ml. Also in the pulp seed box 27, the bacteria count was reduced from $10^7$ CFU/ml to $10^6$-$10^5$CFU/ml. As a result, development of slime was prevented, and the smell of hydrogen sulfide or other smelling material did not occur, which would have occurred in the conventional method.

EXAMPLE 3

The number of public baths, medicinal hot-spring baths and health spas adding herbs or extracts thereof to bath water has increased recently, but partly because of the price of herbs, the bath water has not always been allowed to flow over the bath. As a result, in the conventional method, the bath water could not be kept sufficiently clean as microorganisms and other material bred due to hair and dirt from the added herbs and human bodies. Also fragrance of herbs acted as an ineffective deodorant. As an alternative disinfectant, chlorine or sodium hypochlorite affected eyes and skin and caused discoloration of hair, and in the meantime, medicinal bathwater became dark black in about twelve hours due to decomposition and deterioration of additives or other material.

In Example 3, in order to solve these problems, the testing apparatus was operated with 20 immersion-type electrolyzers 10 arranged in the synthetic resin electrolytic vessel 36, as shown in FIGS. 5A, 5B and 5C. A medicinal hot-spring bath in a men's large bath at a health spa was 24 m³ in volume, 5 m³/hour in circulating flow, and 39° C. in bathwater temperature. Everyday, in the past, the medicinal hot-spring bath was cleaned and herbal bathwater was replaced with fresh bathwater. Further, for disinfecting purposes, a sodium hypochlorite solution was added to the bath water in such a manner that the bath water be 2-3 mg/liter in residual chlorine concentration. The health spa opens at 10 o'clock every morning and closes at 5 o'clock in the morning of the next day.

During three days before operation of the present testing apparatus was started and during eight days after being started, sampling of circulating bathwater was carried out on schedule, and each sample was cultivated for 20 hours on a vegetable gelatin base, whereupon coliform bacilli count examination was made in a predetermined manner. The test results are shown in Table 3. Table 3 indicates that, during three days before the operation of the present test apparatus was started, the residual chlorine concentration was 2-3 mg/l, and every night the bathwater became dark black and gave off a slightly stagnant and chlorine smell, thus making the fragrance of herbs ineffective. On the other hand, during eight days after the operation of the present testing apparatus was started, the residual chlorine concentration was 0.4-1.1 mg/liter, and even at night the medicinal hot-spring bathwater remained unchanged in color and smell as compared to in the morning of the same day.

TABLE 3

Coliform bacillus count during 3 days before the testing apparatus was started

| Date | Sampling timetable | | | | |
|---|---|---|---|---|---|
| | 10 | 12 | 16 | 19 | 24 |
| Sept. | | | | | |
| 2 | 900 | 6,000 | 98,000 | 324,000 | 226,000 |
| 3 | 2,500 | 15,000 | 156,000 | 545,000 | 284,000 |
| 4 | 800 | 3,200 | 61,000 | 89,000 | 306,000 |
| Test Started Sept | | | | | |
| 5 | 0 | 0 | 0 | 0 | 0 |
| 7 | 0 | 0 | 0 | 0 | 0 |
| 9 | 0 | 0 | 3 | 8 | 0 |
| 12 | 0 | 0 | 0 | 0 | 0 |

According to the present invention, the following advantageous results can be achieved.

(a) According to the present invention, an alkaline electrolyte solution mixed of sodium hypochlorite, sodium chloride and sodium bromide is electrolyzed by a diaphragmless electrolyzer 1 to thereby provide electrolytic water, and the provided purging and disinfecting water is used, as purging and disinfecting water, with or without being diluted with service water or other water to be purged and disinfected. Partly because the provided purging and disinfecting water is alkaline, it is possible to enhance the purging and disinfecting effect. Further, it is possible to provide purging and disinfecting water that causes no corrosion of metal parts of the water circulatory system and is harmless to the human body.

In the conventional method using sodium hypochlorite as a disinfectant, the residual chlorine concentration increased commensurate with the amount of the disinfectant, and the disinfecting strength was insufficient. On the other hand, in Example 2, samples of the white liquor for bacteria count examination was obtained at four different locations in the white liquor circulating line. In any sampling position at anytime, no residual chlorine was found. Instead, dirt such as non-biodegradable waste and hair and development of slime were not observed so that clean-out was required on only a few occasions. Also, a slime prevention agent (e.g. Slicon) was not necessary. It is therefore possible to save various costs for unnecessary discharge of white liquor, unnecessary treatment of the increased drain, unnecessary supplemental well water, and redundant chemical additives.

(b) According to the present invention, an alkaline electrolyte solution containing a mixture of sodium hypochlorite and sodium chloride is electrolyzed by a diaphragmless electrolyzer to thereby provide electrolytic water as purging and disinfecting water, and the provided purging and disinfecting water is added to the circulating water in the water circulatory system, so that noxious microorganisms, such as germs, yeasts, fungi, and viruses, growing in the water circulatory system are disinfected and the water circulatory system is purged while the resulting circulating water flows in the water circulatory system. Because a swimming pool, a bath in a hospital or an assisted-living facility, and a spring bath are each already equipped with a circulating water line, the provided purging and disinfecting water can be added to the circulating water with maximum ease.

(c) According to the present invention, it is possible to purge and disinfect the circulating water using electrolyzed water of neutral pH and above as provided using an alkaline electrolyte of caustic sodium carbonate, caustic potassium, phosphorous sodium carbonate or sodium hypochlorite, so that the purging and disinfecting method can be applied to very many kinds of circulating water. Further, it is possible to disinfect noxious microorganisms, such as germs, yeasts, fungi, and viruses growing in the water circulatory system, in which water-soluble organisms and dirty matter are dissolved in the circulating water, and causing decomposition of water and development of slime.

Further, it is possible to eliminate unpleasant smell of decomposed matter in the circulating water by purging the circulating water. More significantly, it is possible to oxidation decompose slime and organic film adhered to surfaces of pipes and tank in the water circulatory system and proliferating as a host or medium for noxious microorganisms, such as Amoebas and Legionella bacillus, thereby purging the circulating water and the water circulatory system.

(d) According to the present invention, partly because the electrolyte solution is made to flow from an electrolyte solution container into the electrolyzer located in an electrolytic water line by an electrolyte solution metering pump, and partly because the electrolytic water is added to the circulating water, it is possible to purge and disinfect water circulatory system equipment, such as a circulating water line and object equipment that uses the circulating water, in addition to the circulating water. Another significant result is that as well as being alkaline, the electrolytic water has a high purging and disinfecting strength.

The present invention is therefore useful when used in a variety of fields. Namely, the circulating water is water for use in air-conditioning, water for absorbing drainage water to be recycled, water in which a water-soluble cutting oil, a water-soluble grinding oil, a water-soluble plastic oil or a coolant is dissolved for metalworking, rinsing water for use in metal coating or surface treatment, water for use in sizing warp yarns of woven cloth, water for use in non-woven cloth treatment, hydrophilous reaction water for emulsion polymerization or pearl polymerization or water for use in processes in a pulp plant or papermaking plant. Necessary additives, starch, chemicals or preserves are dissolved in the circulating water, and microorganisms, such as germs, yeasts, fungi, and viruses, causing degradation and decomposition of water or development of slime, grow in the water circulatory system. It is possible to purge microorganisms, such as germs, yeasts, fungi, and viruses growing in the water circulatory system and causing decomposition of water and development of slime, with scarcely any affect on these added substances, and to decompose and purge dirt such as slime and organic film adhered to the water circulatory system.

(e) According to the present invention, when activated carbon is placed on or in a filter located in the circulating water line, hypohalogenous acid and hypohalogenous acid ions remaining in the circulating water are decomposed through catalytic action to discharge activated oxygen. By such strong oxidation, it is possible to decompose and purge dirty substances and microorganisms in the circulating water which are adhered and adsorbed on the filter and the activated carbon, so that clogging of the filter surface is prevented, thereby minimizing the frequency with which backflow washing is required. Because of this backflow washing, it is possible to save supplementing service water and unnecessary discharge of the circulating water containing valuable matter.

(f) According to the present invention, if the circulating water is bath water, spring water, medicinal bathwater or pool water in which natural substances, bath salts, herbs or extracts thereof are dissolved, it is possible to disinfect microorganisms, such as germs, yeasts, fungi, and viruses, growing in the circulating water system in which water-soluble organics such as dirt removed from a human body and dissolved in the circulating water and causing degradation or decomposition of water or development of slime. It is also possible to decompose and purge water-soluble organisms, such as dirt and hair removed off the human body and dissolved in the circulating water.

(g) According to the present invention, the circulating water is soil cleaning water for washing soil contaminated with noxious substances, such as agrichemicals, trichloroethylene or dioxin, and the contaminated soil is washed so that the noxious substances are washed out or extracted in the soil cleaning water. It is therefore possible to purge the resulting soil cleaning water by oxidation decomposing the noxious substances by electrolysis so that the purged soil cleaning water can be safely drained or repeatedly used.

(h) According to the present invention, an alkaline electrolyte solution comprising a mixture of sodium hypochlorite and sodium chloride is made to flow from an electrolyte solution container into an electrolyzer by an electrolyte solution metering pump to thereby provide the electrolytic water, and the provided electrolytic water is added to circulating water in an existing water circulatory system. It is thereby possible to disinfect microorganisms, such as germs, yeasts, fungi, and viruses, growing in the water circulatory system and causing degradation and decomposition of water and development of slime. Partly because the present apparatus is compact in size and can be easily installed in a small space, and partly because not much redundant piping is needed, the present invention is useful for the facility management who seeks to enhance purging and disinfecting of circulating water in the existing facility with reduced cost.

(i) By evaporation coating conductive ceramics or a conductive metal with a film of conductive ceramics or a film of conductive diamond, it is possible to provide a high-corrosion-resistant anode. With this anode, because effective electrolysis can be carried out at a high current density, it is possible to provide an electrolyzer compact in size and high in electrolyzing performance. Because of high current density, hypohaloid acid and activated hydrogen, particularly hydroxy radicals, can be generated in an efficient electrolysis and hence the circulating water can be purged and disinfected without affecting high-molecular-weight organisms, such as starch and pulp.

The present invention is useful when used in purging and disinfecting a wide variety of kinds of water, such as water in an air-conditioning system or a waste gas scrubber, combined treatment water for recycling drain water, water in which a water-soluble cutting oil, a water-soluble grinding oil, a water-soluble plastic oil, coolant, etc. is dissolved for metalworking treatment, rinsing water in metal coating or surface treatment, water in sizing warp yarns of woven cloth, water in treating non-woven cloths, hydrophilous reaction water for emulsion polymerization and pearl polymerization, water for use in processes in a pulp plant or a papermaking plant, water for use in food-making processes, such as rinsing and washing tofu, various types of noodles, macaroni, butcher's meat such as ham and sausage, egg, fish and shellfish, crops, bed linens and clothing, hot spring water, medicinal bath water, pool water or other water for use in a plant, home or public facility environment for humans or animals, such as a medical center or a food manufacturer.

What is claimed is:

1. A method of producing purging and disinfecting water, comprising the steps of:
   providing an aqueous alkaline electrolyte solution comprising a mixture of an alkaline electrolyte and a neutral salt; and
   electrolyzing the aqueous alkaline electrolyte solution using a diaphragmless electrolyzer to thereby produce alkaline electrolytic water, wherein, the aqueous alkaline electrolyte solution is made to flow from an electrolyte solution container into an electrolyzer located in an electrolytic water line by an electrolyte solution metering pump, and the resulting electrolytic water is added to circulating water in a water circulatory system.

2. The method according to claim 1, and including the step of diluting the resulting purging and disinfecting water with water.

3. The method according to claim 1, wherein the aqueous alkaline electrolyte solution comprises a mixture of at least one aqueous alkaline electrolyte selected from the group consisting of caustic sodium carbonate, caustic potassium carbonate, phosphorous sodium carbonate and hypochlorous acid soda, and at least one neutral salt selected from the group consisting of sodium chloride, potassium chloride, sodium bromide and potassium bromide.

4. The method according to claim 1, wherein the water circulatory system comprises an air-conditioning system, a metal working or metal treating system, a textile treating system, an emulsion polymerization or pearl polymerization system and a pulp plant or papermaking system.

5. The method according to claim 1, wherein an activated carbon filter unit is located in the water circulatory system whereupon any hypohaloid acid and hypohaloid acid ions in the circulating water may be decomposed through catalytic action, and dirt and microorganisms in the circulating water which may become adhered and adsorbed on the filter are decomposed and purged by oxidation.

6. The method according to claim 1, wherein the circulating water comprises bath water, spring water, medicinal bathwater or pool water in which one or more of the following substances may be present: natural substances, bath salts, herbs, germs, yeasts, fungi, viruses and organic matter removed from a human body.

7. The method according to claim 1, wherein the circulating water comprises water for washing soil contaminated with noxious substances selected from agrichemicals, trichloroethylene and dioxin, and the contaminated soil is washed so that the noxious substances are washed out or extracted in the soil cleaning water, and the resulting soil cleaning water is purged by oxidation decomposing noxious substances therein by electrolytic action.

8. An apparatus for purging and disinfecting water, comprising:
   an electrolyte solution container for storing an aqueous alkaline electrolyte solution comprising a mixture of an alkaline electrolyte and a neutral salt;
   an electrolyzer for electrolyzing the aqueous alkaline electrolyte solution to thereby provide alkaline electrolytic water as purging and disinfecting water;
   a metering pump for pumping the electrolyte solution from said electrolyte solution container to said electrolyzer for electrolysis;
   a circulating water line having a circulation pump; and
   a pump for adding alkaline electrolytic water from the electrolyzer to the circulating water.

9. The apparatus according to claim 8, wherein said electrolyzer includes an anode of conductive ceramics or a conductive metal evaporation coated with a film of conductive ceramics or a film of conductive diamond, a cathode of a conductive material, and an inter-electrode reaction section, and wherein aqueous alkaline electrolyte solution from said electrolyte solution container is delivered to the electrolyzer by a metering pump where the aqueous alkaline electrolyte solution is electrolyzed to provide alkaline electrolytic water, and the resulting alkaline electrolytic water is added to circulating water to purify the circulating water.

* * * * *